United States Patent [19]

Simone et al.

[11] Patent Number: 5,190,743

[45] Date of Patent: Mar. 2, 1993

[54] COMPOSITION FOR DISCLOSING DENTAL PLAQUE

[75] Inventors: Alexander J. Simone; Thomas G. Polefka, both of Somerset, N.J.

[73] Assignee: Colgate-Palmolive Company, New York, N.Y.

[21] Appl. No.: 774,494

[22] Filed: Oct. 10, 1991

Related U.S. Application Data

[62] Division of Ser. No. 696,404, May 6, 1991, Pat. No. 5,098,691.

[51] Int. Cl.$^5$ .......................... A61K 7/16; A61K 7/22; A61K 49/00
[52] U.S. Cl. ....................................... 424/7.1; 424/49; 424/54; 514/52
[58] Field of Search .................... 424/49–58, 424/7.1; 514/52

[56] References Cited

U.S. PATENT DOCUMENTS

| | | | |
|---|---|---|---|
| 4,069,311 | 1/1978 | Mannara | 424/49 |
| 4,069,312 | 1/1978 | Mannara | 424/49 |
| 4,259,355 | 3/1981 | Marmo et al. | 424/49 |
| 4,432,975 | 2/1984 | Libby | 514/52 |
| 4,565,701 | 1/1986 | Ferguson | 426/72 |
| 4,618,489 | 10/1986 | Pollock et al. | 424/49 |
| 4,639,368 | 1/1987 | Niazi et al. | 424/48 |
| 4,861,582 | 8/1989 | Pollock et al. | 424/49 |
| 5,098,691 | 3/1992 | Simone et al. | 424/7.1 |

FOREIGN PATENT DOCUMENTS 2206873  8/1973  Fed. Rep. of Germany.
1279214  6/1972  United Kingdom.

OTHER PUBLICATIONS

Kolhler C.A. 80:6916B (1973) of Ger. DE. 2206873 (Aug. 23, 1973).
Forest Labs GA. 77:105623y (1972) of GT. BR 1279214 (Jun. 28, 1972).

Primary Examiner—Shep K. Rose
Attorney, Agent, or Firm—Paul Shapiro; Robert C. Sullivan

[57] ABSTRACT

Plaque disclosing compositions containing a cobalamin compound such as Vitamin $B_{12}$ as the disclosant and the process of treating the oral cavity therewith.

4 Claims, No Drawings

COMPOSITION FOR DISCLOSING DENTAL PLAQUE

This application is a divisional application of prior application 07/696,404 filed May 6, 1991 now U.S. Pat. No. 5,098,691.

BACKGROUND OF THE INVENTION

1. Field of Invention

This invention relates to plaque disclosing compositions containing a cobalamin compound for use as a diagnostic tool and in the improvement of oral hygiene practices.

2. Disclosure of the Prior Art

A significant portion of dental plaque which forms on tooth surfaces consists of colonies of bacteria surrounded by a matrix of polysaccharide and protein which cannot be flushed away by simply rinsing with water. Active brushing of the teeth is required to remove the adherent plaque.

It is a well accepted fact that dental plaque when allowed to accumulate on tooth surfaces can eventually lead to gingivitis, periodontal disease, caries and calculus. Thus, it is apparent that effective removal of deposits of dental plaque is absolutely essential for oral health. Accordingly, proper oral hygiene practices which may be carried out by an individual on his or her own teeth or by a dentist, necessitates readily available means of identification and location of plaque deposits in the oral cavity.

Since dental plaque is usually transparent and colorless and not easily visible, an individual frequently is not aware of the quantity or the location of dental plaque present on the teeth. Therefore, it is desirable to use plaque-disclosing compositions to identify tooth areas where plaque buildup is a problem. The use of disclosing compositions motivate a person in the early removal of dental plaque by showing the presence and quantity of plaque.

Disclosing agents for dental plaque as a means of measuring tooth cleanliness and to effect proper oral hygiene practices, have been widely explored in the prior art.

Disclosing agents include organic dyes such as erythrosin (FDC Red #3) as disclosed in U.S. Pat. No. 3,309,274 by Brilliant, and U.S. Pat. No. 3,624,219 by Perlitsch. Block patents U.S. Pat. Nos. 3,723,613; 3,997,658 and 4,064,229 disclose a two-tone dye test comprising the combination of the erythrosin with either FDC Green #3, FDC Blue #1 or Hercules Green Shade 3 in order to obtain differential staining, i.e. thick old plaques stain blue and thin new plaques stain red.

Gaffar, U.S. Pat. No. 4,431,638, discloses a red vegetable dye obtained from sugar beets as a plaque disclosant. Kosti, U.S. Pat. No. 4,348,378 discloses rupturable microencapsulated dyes as a plaque disclosant. Frysh, U.S. Pat. No. 4,666,700 discloses as a plaque disclosant a water insoluble pigment such as a lake.

A drawback to the use of the plaque disclosing dyes and pigments of the prior art is that they normally have an unpalatable and objectionable taste which is not effectively masked by any known flavoring agent or sweetener and these colorants indiscriminately stain surfaces including the tongue, lips and clothing of the user.

SUMMARY OF THE INVENTION

It has been found that cobalamin compounds and particularly cyanobalamin (Vitamin $B_{12}$) disclose plaque as effectively as any of the prior art dyes and pigments with the additional advantages of being non-staining to all other surfaces, being odorless and tasteless, as well as being safe for oral use. Vitamin $B_{12}$ containing plaque disclosing products stain only dental plaque and can be easily rinsed from the mouth once applied to the teeth. Accordingly, the present invention relates to dental plaque disclosing compositions containing an effective staining amount of a cobalamin compound in a physiologically acceptable vehicle, which may be in the form of a rinse, gel, tablet or powder.

DESCRIPTION OF THE PREFERRED EMBODIMENTS

By the term "cobalamin" is meant the compound cyanocobalamin (Vitamin $B_{12}$) and like compounds, for example hydroxycobalamin (Vitamin $B_{12b}$), which is converted to cyanocobalamin by the action of cyanide ions and Vitamin $B_{12c}$ which is prepared by treating Vitamin $B_{12b}$ with nitrous oxide.

Vitamin $B_{12}$ is preferred for use in the practice of the present invention.

Vitamin $B_{12}$, isolated in the form of hydroscopic dark red crystals, is a naturally occurring cobalt containing compound found in soil and water and produced by intestinal microorganisms. Vitamin $B_{12}$ is designated by the FDA as "generally recognized as safe" when used in accordance with good manufacturing practices and may be added directly to human food (21 CFR 184.1945).

When used as a plaque disclosant, Vitamin $B_{12}$ binds to or becomes trapped in the plaque matrix and stains the plaque red so that it becomes clearly visible on the tooth surface. After use, the red stain is easily rinsed off from tooth surface.

Accordingly, the presence of the Vitamin $B_{12}$ in a plaque-disclosing composition renders the plaque deposits on the teeth clearly and selectively visible to the user immediately upon contact therewith, and persists on the surfaces to the degree desirable for plaque-disclosing purposes; but does not exhibit any staining effect on any other surface in the mouth. The stain is easily removed from the teeth by simple rinsing, is odorless, tasteless and non-toxic, thereby providing an effective tool for diagnostic use and in self-help oral health programs.

Cobalamin compounds such as Vitamin $B_{12}$ may be incorporated in a disclosing composition in a variety of ways. One method is to incorporate the Vitamin $B_{12}$ into a mouthrinse composition, which is used to rinse the mouth prior to examining it for plaque deposits. Alternatively, Vitamin $B_{12}$ may be incorporated into a gel or a chewable tablet, powder or lozenge or other solid or semi-solid product.

Mouthrinses for use as plaque disclosing agents can contain any amount of Vitamin $B_{12}$, but advantageously, due to cost considerations, the mouthrinse generally contains about from 0.1 to 5% by weight Vitamin $B_{12}$.

Mouthrinse compositions which have been found useful for the practice of the present invention generally comprise water, such as deionized water as the vehicle and, optionally, other ingredients such as non-toxic alcohols such as ethanol, flavors, stabilizing agents, sweeteners, and humectants such as glycerine and sorbitol. Stabilizing agents incorporated into the products of the present invention include synthetic anionic linear polymeric polycarboxylates which are employed in the form of their partially or preferably fully neutralized water soluble alkali metal (e.g. potassium and preferably sodium) or ammonium salts. Preferred are 1:4 to 4:1 copolymers of maleic anhydride or acid and a polymerizable ethylenically unsaturated monomer, preferably a lower alkyl vinyl ether such as methoxyethylene, having a molecular weight of about 30,000 to about 1,000,000 available commercially from GAF Corporation under the trademark Gantrez. The stabilizing agents are incorporated in the plaque disclosing mouthrinse compositions of the present invention at a concentration of about 0.1 to about 5% by weight and preferably about 0.3 to about 1.0 percent by weight.

Vitamin $B_{12}$ may also be incorporated in gels, pastes or powders that are topically applied or in the form of chewable tablets that can be chewed by the patient to apply the disclosing composition.

Solid and semi-solid plaque disclosing agents including gels, pastes, powders, tablets and lozenges and the like can incorporate 0.1 to 10% by weight Vitamin $B_{12}$ as well as optional ingredients. Higher levels of Vitamin $B_{12}$ may be used, but again the cost of the compounds dictates that the lowest effective concentration be used. Optional ingredients used in the preparation of solid and semi-solid products include, for example, as the vehicle, a humectant such as glycerine, sorbitol, polyethylene glycol, generally in the amounts up to about 20.0 percent by weight, and preferably from about 5.0 to about 20.0 percent by weight. Additional additives include, but are not limited to a non-toxic alcohol such as ethanol at a concentration of about 3 to about 15 percent by weight and preferably about 5 to about 10 percent by weight, a thickener or gelling agent such as polyvinylpyrolidone, hydroxyethyl propylcellulose, hydroxybutyl methyl cellulose, hydroxypropyl methyl cellulose, hydroxyethyl cellulose, sodium carboxymethyl cellulose and the like, at a concentration of about 0.05 to about 1.0 percent by weight and preferably about 0.1 to about 0.5 percent by weight and a surfactant such as polyoxyethylene-polyoxypropylene block polymers available under the tradename "Pluronics", an amido betaine such as cocoamido propyl betaine and water soluble salts of higher fatty acid monoglyceride monosulfates, such as sodium salts of the monosulfated monoglycerides, or hydrogenated coconut oil fatty acids, higher alkylsulfate, such as sodium lauryl sulfate and alkyl aryl sulfonates, such as sodium dodecyl benzene sulfonate, the surfactant being present at a concentration of about 0.1 to about 2.0 percent by weight and preferably about 0.5 to about 1.5 percent by weight. A natural or synthetic sweetening agent such as dextrose, levulose, saccharin, or cyclamate as well as flavors such as oils of spearmint, peppermint, wintergreen, may be included in the solid or semi-solid product at a concentration of about 0.01 to about 2 percent by weight of the product. In addition to the other optional ingredients, tablets may contain inert additives which help to impart satisfactory compression characteristics to the formulation including diluents, binders and lubricants. Any known carrier or diluent which is stable and compatible with and does not adversely affect the plaque disclosing properties of cobalamins such as Vitamin $B_{12}$ can be utilized, such as dicalcium phosphate, calcium sulfate, lactose, kaolin, sodium chloride, dry starch, or the like, and mixtures thereof. The carrier or diluent constitutes the major ingredient of the tablet formulation and is present in amounts of about 40 to 95%, and preferably about 70 to 95% by weight.

Another ingredient generally contained in a tablet is a lubricant which prevents adhesion of the tablet materials to the surface of the dies and punches, reduces interparticular friction during compression, and facilitates the ejection of the tablet from the die cavity. Again, compatibility with the cobalamin such as Vitamin $B_{12}$ is the essential prerequisite. Suitable lubricants include magnesium stearate, calcium stearate, paraffin, stearic acid, cocoa butter, and talc. The proportion of lubricant is generally in the range of about 0.1 to 5% by weight. The present invention is further illustrated by the following Example:

EXAMPLE

A study was conducted to quantitatively assess the plaque disclosing efficiency of a Vitamin $B_{12}$ plaque disclosing rinse and gel composition using computer-enhanced, digitized photography. The Vitamin $B_{12}$ plaque disclosing gel and rinse products used in this study are fully identified below.

Eight panelists used each gel and rinse product once and had baseline photographs taken of their teeth prior to using each product. The panelists used 10 milliliters of the plaque disclosing rinse and 1.0 gram of the gel product. These products stained the teeth of the panelists red, but did not stain any other mouth areas. The product remained in contact with the panelists' teeth for 1 minute before it was easily rinsed away. Photographs were taken between application of the products to assure wash-out of the previous Vitamin $B_{12}$ product. Depending on the panelist, 21-24 teeth were scored for plaque area. Scores were compiled and adjusted for the number of teeth. Photographs of the panelists' teeth were converted to a digital image on a computer. The red stained tooth areas of each panelist identified to the computer were converted into numerical units of area and the units totaled. The adjusted plaque scores for each panelist as well as the adjusted averages for the entire panel are summarized in the Table below.

| PLAQUE DISCLOSING VITAMIN $B_{12}$ GEL FORMULA | |
|---|---|
| | % by Weight |
| Water | 75.77 |
| Glycerine | 10.00 |
| Ethyl Alcohol | 8.00 |
| Vitamin $B_{12}$ | 5.00 |
| Pluronic F - 108 | 1.00 |
| Carboxyvinyl Polymer (Carbopol) | 0.20 |
| Sodium Saccharin | 0.03 |
| | 100.00 |
| PLAQUE DISCLOSING VITAMIN $B_{12}$ RINSE FORMULA | |
| | % by Weight |
| Water | 92.87 |
| Gantrez S-97 (~13%) | 5.95 |
| Vit. $B_{12}$ | 1.00 |
| Flavor | 0.18 |
| | 100.00 |

TABLE 2

| PRODUCT | PANELIST | NO. TEETH EXPOSED | ADJ. PLAQUE AREA % OF TOOTH COVERED | MEAN PLAQUE AREA % OF TOOTH COVERED |
| --- | --- | --- | --- | --- |
| Vitamin $B_{12}$ Gel | 1 | 23 | 15.57 | 13.2 |
|  | 2 | 22 | 11.23 |  |
|  | 3 | 22 | 9.10 |  |
|  | 4 | 23 | 12.68 |  |
|  | 5 | 21 | 12.58 |  |
|  | 6 | 22 | 7.78 |  |
|  | 7 | 23 | 18.77 |  |
|  | 8 | 24 | 17.28 |  |
| Vitamin $B_{12}$ Rinse | 1 | 23 | 12.13 | 7.9 |
|  | 2 | 22 | 6.56 |  |
|  | 3 | 22 | 6.26 |  |
|  | 4 | 23 | 10.98 |  |
|  | 5 | 21 | 11.81 |  |
|  | 6 | 22 | 4.61 |  |
|  | 7 | 23 | 4.68 |  |
|  | 8 | 24 | 6.81 |  |

The data in the Table indicate that the Vitamin $B_{12}$ rinse and gel products readily disclosed plaque. This was accomplished without the taste and staining problems normally encountered with prior art dyes and pigments. Both Vitamin $B_{12}$ gel and rinse products were easily washed out from the oral cavity with a single water rinse.

By way of comparison, the above study was repeated using a typical commercially available plaque disclosing rinse. This commercial rinse scored in the range of 10-20% of tooth covered but suffered from the drawback of indiscriminate staining of surfaces.

What is claimed is:

1. A plaque disclosing aqueous rinse composition containing an effective staining amount of a cobalamine compound which is absorbable by plaque deposits to identify areas of plaque formation on teeth which are clearly visible to the naked eye as color stained plaque immediately upon contact and easily removable therefrom by rinsing.

2. The composition of claim 1, wherein the cobalamin compound is Vitamin $B_{12}$.

3. The composition of claim 1, wherein the disclosing composition is in the form of a gel.

4. The composition of claim 1, wherein the cobalamin compound is present in the composition at a concentration of about 0.1 to about 5.0% by weight.

* * * * *